Figure 1:
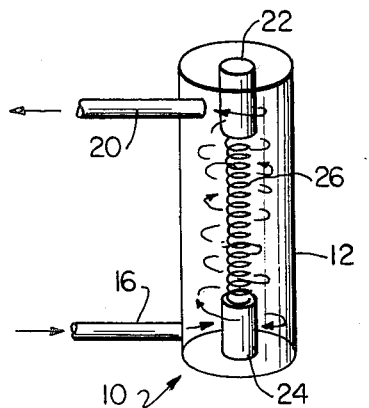

United States Patent [19]

Lawson et al.

[11] 4,215,564

[45] Aug. 5, 1980

[54] MINIATURIZED THERMAL CONDUCTIVITY DETECTOR

[75] Inventors: Alexander E. Lawson, Mendham; Robert J. Mathieu, Mountain Lakes, both of N.J.

[73] Assignee: Gow-Mac Instrument Co., Bound Brook, N.J.

[21] Appl. No.: 9,949

[22] Filed: Feb. 6, 1979

[51] Int. Cl.$^2$ .................................................. G01N 25/00
[52] U.S. Cl. ................................................. 73/27 R
[58] Field of Search ..................................... 73/27 R

[56] References Cited

U.S. PATENT DOCUMENTS

| | | | |
|---|---|---|---|
| 2,306,509 | 12/1942 | Talmey | 73/27 X |
| 3,621,707 | 11/1971 | Kolloff et al. | 73/27 |
| 3,791,195 | 2/1974 | Loe | 73/27 |

Primary Examiner—Herbert Goldstein
Attorney, Agent, or Firm—Fidelman, Wolffe & Waldron

[57] ABSTRACT

A hot wire miniaturized thermal conductivity detector with a cavity volume less than 50 microliters characterized by a construction which provides for essentially plug flow through a cylindrical cavity. The gas flows tangentially into and out of toroidal passageways presented between axial filament mounts and the cylindrical cell wall so that the gas flow-passage area increases by stages as the gas flows from an inlet into the detector cavity first through the toroidal passageways therein then through the main body thereof. Correspondingly the flow path decreases by stages from the main body into the toroidal passageway then into the outlet.

Preferably the passage area increase from inlet to main body is held to less than a five fold increase in area.

3 Claims, 4 Drawing Figures

MINIATURIZED THERMAL CONDUCTIVITY DETECTOR

INTRODUCTION

Over the years, the performance of gas chromatographic (GC) columns have been improved to the point where capillary columns now available to the art have more than 50,000 theoretical plates.

Such GC column capabilities raise the question of whether column capabilities have gone beyond the resolution achieved by the detector systems available to the art for use with CG columns, notably flame ionization detectors (FID), electron capture detectors (ECD), flame photometric detectors (FPD) and thermal conductivity detectors (TCD). Investigations by workers in the art established that the lower capability packed CG columns previously employed by workers in the art rarely pushed the detection limits of FID, ECD, FPD, but did operate at about the detection capabilities of the TCD. Indeed even when the internal volume of a TCD was greatly reduced from what had been prevelant theretofore (in effort to improve sensitivity), the Thermal Conductivity Detector (TCD) measured out to be about 100-fold less sensitive than the flame ionization detector (FID). (See "Performance of a Reduced Volume Thermal Conductivity Detector", Pecsar etal., Anal Chem Vol 45, No. 13, November 1973, pp. 2191-2198).

In consequence the hot wire type TCD available to the art turns out to be a poor match for capillary gas chromatography columns, because the hot wire thermal conductivity detectors provide readings far more gross than the capabilities of capillary column chromatographic separation for any composition from which the CG result is an eluant carrier gas containing numerous major and minor components in close together band volumes. The minor component may be misread or missed altogether by the hot wire TCD instrument.

There has occurred a significant shift in relative usage away from TCD systems to the FID, ECD, FPD, systems, despite the numerous desirable characteristics unique to TCD systems. As compared to FID for example, the TCD employs less complex electronics, is a nondestructive test, and is of wider applicability (e.g. applicable to analysis of inorganic materials). Manifestly, a TCD system approximating in sensitivity the sensitivity of the FID system would be of great value to the art.

BACKGROUND OF THE INVENTION

The usual hot wire TCD (thermal conductivity detector) comprises a metallic block containing one or more cylindrical cavities through which the gas stream under test flows. A heated element, notably an electrically heated resistance wire positioned inside the cavity, looses heat to the block at a rate depending upon the thermal conductivity of the gas therein, which in turn changes wire temperature and wire resistance. The changes in wire resistance are measured.

The TCD is a concentration dependent system, and if the gas volume containing a GC component is increased after leaving the GC column through dilution of the component in more carrier gas, the reduced concentration of component due to such band broadening detrimentally affects the TCD system. Unfortunately passage of gas through the detector itself introduces variences that contribute to the band broadening effect.

A detailed discussion of the variances attributable to cell volume and cell design has been provided concurrently with the genesis of this invention by Lochmuller et al. in J. of Chromatographic Science, Vol. 15, pp. 285-289, (August 1977).

RATIONALE OF THE INVENTION

While attainment of about a hundred-fold improvement of sensitivity of the TCD system through improved structure might seem to be an outsized ambition, the objective is no less. Fortunately the concentration dependent character of the TCD magnifies the effect of whatever improvements can serve to reduce band broadening.

Thus one basic object of this invention is to provide the cell cavity and flow connections for a hot wire TCD system which causes flow of the carrier gas therethrough to be with little band broadening inside the detector attributable to the detector.

The art has investigated the concepts involved in thermal conductivity detection and suggested many diverse structures for hot wire TCD systems including for example, flow through designs, semi-diffusion designs, and diffusion designs, and has studied the effects of cavity volume on the accurancy of thermal detector instruments. Yet suprisingly little effort has been directed to how cell details add to or detract from the overall quality of the hot wire flow through TCD detector as an instrument, i.e. on the resolution capabilities and sensitivity of the TCD system. Prior workers in the art have, of course, made valuable suggestions for improving particular features of the cell, including for example a suggestion for providing tangential gas inlet to and outlet from the cell cavity as can be found in U.S. Pat. No. 3,474,660 and, separately by the suggestion of reducing the cavity size to a practical minimum as can be found in Pecsar et al, supra.

Despite the incorporation of such improvements the flow-through hot wire TCD, to which this invention relates, compares poorly to the FID even when care is taken to operate at optimum flow rate and with careful calibration. The inventors herein concluded that the cavity structures must contain features detrimental to the quality of the TCD system.

The cavity structure might contain cavity regions outside the flow path of the gas therethrough i.e. dead space and/or an excessively large jump in flow path area for the gas from that of the narrow channel of the entrance tube to the flow path inside the cavity, the latter possibly creating dead space regions. One location inside the cavity which could be dead space in that portion of the center of the cavity axially of the tangential entrance. The cavity structure of the present invention fills in those portions of the cavity volume that otherwise might be dead space, and in addition provides for changing the gas flow path area into and through the cavity to a staged increase and a staged decrease. Some confirmation for the correctness of the rationale of this invention is provided by computation of the Reynolds No. in the TCD cavity as being less than 1, a value representative of eddy-free laminar flow.

It may be noted that an important objective herein is to provide the art with a practical improvd TCD, i.e. a TCD manufacturable without prohibitive expense. The inventors herein have found it possible to make a small sized cavity with state of the art manufacturing techniques and commercially available components.

BRIEF STATEMENT OF THE INVENTION

Briefly stated the hot wire TCD cell of the present invention comprises a cylindrical cavity of less than 50 microliters in volume with a tangential entrance adjacent one end face of the cavity and a tangential exit adjacent the other end face of the cavity. One filament mount or filament pin (often termed pin hereafter) extends axially of the cylinder into the cavity from an end face to a point axially of the cylinder beyond the tangential gas inlet entrance opening and a second filament mount extends axially of the cylinder into the cavity from the opposing end face to a point axially of the cylinder beyond the tangential gas outlet opening. The filament, preferably a coil wound filament, extends axially of the cylinder from filament mount to filament mount. Thus, the entrance to, and the exit from the cylindrical cavity are torodial or donut shaped regions wherein the filament and (filament) pins fill what is believed to be a relatively stagnant space in the cavity formed by the vortical flow pattern of the gas passage through the cylindrical cavity.

The gas passage channel area, i.e. the cross-section area, through the cavity increases by stages then decreases by stages. For example the flow channel area doubles between the inlet tube and the toroidal entrance region in the cylindrical cavity, then doubles again inside the main body of the cavity, and, of course, thereafter is halved at the toroidal exit region and again halves at the outlet tube. Preferably, the cavity structure provides for less than a five fold total expansion from the inlet tube passage area to the cross-sectional area of the cavity.

A hot wire TCD constructed according to practice of this invention evidenced a sensitivity quite close to the sensitivity of an FID system.

DETAILED DISCUSSION OF THE INVENTION

Figure 2:
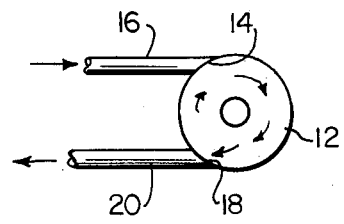
Figure 3:
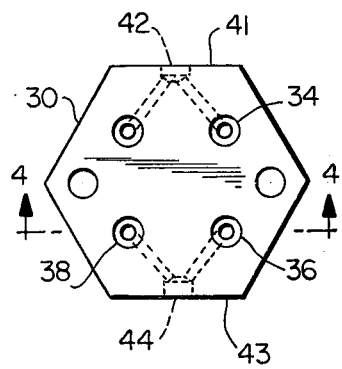
Figure 4:
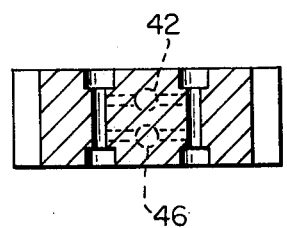

For further understanding of this invention, reference is now made to the drawings wherein:

FIG. 1 is a schematic diagramatic view of the structure of the present invention, FIG. 2 is a plan view of the device of FIG. 1, FIG. 3 is a plan view of a TCD block for a four cavity thermal conductivity detector; and FIG. 4 is a cross-section view taken along line 4—4 of FIG. 3.

Referring now to FIGS. 1 and 2 of the drawing, it may be seen that the TCD cell cavity 10 of the present hot wire thermal conductivity detector system is in the form of a cylindrically shaped cavity 12 having a tangential opening 14 adjacent one end face thereof to which gas inlet tube 16 connects. Correspondingly, adjacent the other end face of cavity 12 is a tangential opening therein 18 to which gas outlet tube 20 connects. Extending axially into cylindrical cavity 12 from one end thereof is one filament mount, a pin 22, which arbitrarily is herein termed the upper filament mount. Extending axially into the other end of the cylindrical cavity 12 is the lower filament mount a pin 24. The filament mount 22 extends into cavity 12 to a point well past the outlet opening 18, and the filament mount 24 extends into cavity 12 to a point well past the inlet opening 14. Disposed between pins 22, 24 and supported between them axially of cavity 12 is a filament 26. Filament 26 is, preferably, the usual coil wound filament employed heretofore in hot wire TCD systems.

The spiral flow of gas from inlet tube 16 entering through tangential opening 14 up through cavity 12 then out tangential opening 18 to outlet tube 20 is indicated in FIG. 1. It is believed that such a flow pattern in a completely empty cylindrical cavity would create a vortex center relatively stagnant region adjacent the end faces of cavity 12 axially of openings 14 and 18. According to practice of the present invention the potentially dead space volume has been filled in by pins 22 and 24. In effect then, the gas enters and leaves cavity 12 through a torodial or donut shaped region inside the cylindrical cavity without forming a vortex. The toroidal entrance portion terminates at a level in cavity 12 beyond the point therein where any vortex would close to form a smooth helical flow pattern, then the flow area again increases and the gas spirals around axial filament 26. Thereafter the gas flow path squeezes down to a toroidal path and at tangential outlet opening 18 the helical gas flow pattern terminates without having formed a vortex.

On the whole, the structure described above is intended to reduce nearly to zero any band broadening of the GC separated components in the thermal conductivity detector, so that the band volume of each of the various components separated by the chromatographic column remains close to the band volume existing at the outlet of the chromatographic column. In this connection it is noted once again that the cavity volume of cell 10 is less than 50 microliters, and preferably is less than 25 microliters; the detector has been miniaturized materially from commercially available prior hot wire TCD instruments as part of the practice of this invention.

The dimensions of cavity 12 and of the cell components associated therewith are significant to a preferred mode of the present invention, wherein a major objective is, of course, to manufacture the improved hot wire TCD available to the art at a reasonable cost.

The practical consideration involved in actually fabricating the TCD of this invention can best be understood in connection with the details of construction of a TCD cell cavity. Therefore, for further understanding of the present invention, reference is now made to FIGS. 3 and 4 which show how the thermal conductivity detector cavity of the present invention may be machined into a block of metal, the illustration being of a four cavity system, a usual mode of TCD instrument.

As can be seen in FIG. 3, a hexagonal shape block 30 has drilled therethrough top to bottom four appropriately sized apertures 32, 34, 36, and 38 e.g. 1/16". The top and bottom portions of each aperture are tapped e.g. to ¼", as shown by FIG. 4 for threading or otherwise setting the pins 22, 24 (not shown) therein leaving a cavity e.g. 0.300" (7.62 mm) in length. A pair of Y shaped gas passages 42, 44 are drilled, e.g. by a #58 drill (which is 0.042", i.e. 1.67 mm), into each opposing side face 41, 43 of block 30, passage 42, 44 are angled to intersect the cavities tangentially as is illustrated in FIG. 3 for gas passage 42, and in FIG. 4 for the passages 44, 46 into face 41, the fourth passage not being shown in the drawing, (Any off-center intersection is effectively a tangential opening.) The Y juncture of each set of gas passages is tapped for threading fittings for appropriate sample gas inlet and outlet lines into block 30.

It should be appreciated that the filament mounts and a filament will be set into each of the four cavities in block 30 to create the TCD cell schematically illustrated in FIG. 1, that the usual electrical connections will be added, and that appropriate sample gas inlet and outlet lines will connect to the four side face openings in the completed instrument.

The cavity volume in each cell of the above described preferred embodiment is about 15 microliters.

The rationale of the exemplary dimensions provided above is to adapt the concepts of the present invention (i.e. staged expansion in flow area and tangential gas entrance into toroidal region) to coil wound filaments available readily, and to (filament) pins available readily, and, also, to (small) standard drill sizes, good machining practices, reasonable tolerances etc. Thus the filament pins may be 3/32" (2.38 mm) long and 0.736 mm in diameter; the coil is an 0.001" wire wound to about 0.356 mm coil diameter. The gas flows through an entrance passageway 47 which is 0.042" or 1.067 mm in diameter, (0.894 mm in area) then enters adjacent the cavity end face into a toroidal region in the cavity disposed between the pin (0.736 mm diameter) and the cavity wall (1.578 mm diameter) which for example is about 2.5 mm$^2$ in cross-section area. The gas flows then into the main cavity which for example is about 3.68 mm$^2$ in cross-section, for a first stage flow expansion area to less than three fold, followed by a second stage flow expansion area to less than five fold in the main body of the cavity 31. The gas then flows out by way of the toroidal region at the other end of cavity 31 through corresponding staged contractions in flow area to outlet passage 49.

The real expansion in flow channel area for the gas in the cavity is far less than the four to five fold described above, because the Reynolds No. (1) of the flowing gas is far down in the laminar flow region. In fact no expansion in flow area may take place. The gas passes from an inlet tube about 1 mm in diameter into a toroidal region wherein the gap between the pin and cavity wall is not quite ½ mm and then travels through cavity 12 under spiral flow circumstances. Treating the spiral flow path as if it were a confined spiral coil of essentially constant cross-section, then such path must flatten elliptically at the entrance to a (minor) axis diameter of about ½ mm, and perforce stretch to a (major) axis diameter of about 2 mm. At the main body portion of the cavity, i.e. between filament mounts the path can round out to about 0.6 mm by 1.5 mm. The exemplary cavity is large enough for only about a four coil spiral. Aside from forcing the gas to fill and flow through what otherwise might still be dead space inside the cavity through changes in coil diameter, the number of coils (vis a vis prior art cavities) has been reduced, reducing also the coil to coil interface area across which component diffusion may occur, a factor that could help explain why significantly reduced band broadening takes place in the TCD of this invention than in prior art TCD systems.

For further appreciation of the present invention, comparative example test results achieved by the structure described above and by a standard commercially available thermal conductivity detector are hereinafter provided. A flame ionization detector was also employed for comparision purposes.

A Varian 3700 GC equipped with an auto linear programmer and dual flame ionization detectors were used with a Gow-Mac 10-952 cell whose internal volume was 160 ml per cavity and with the 4-cavity cell construction described in connection with FIGS. 3 and 4 and dimensioned as described above. The particular Gow-Mac cell used also had tangential gas entrance to and gas exit passages from each cell cavity.

The cells were kept at constant temperature in a tight-fitting aluminum block utilizing the 3700 detector temperature controller. The (Wheatstone) bridge circuit was a Gow-Mac Power Supply Control Unit, Model #40-001.

The injector was a SGE "splitless" (SGE, Austin, Texas). The helium carrier gas flow rate was controlled by two pressure regulators and a variable (0–10 ml/min) flow controller (Model 1000, Porter Instrument Co., Hatfield, PA.). The carrier gas flow rates were determined by a soap bubble flow meter and gas flow rates of 1–10 ml/minute were employed in the test series.

The capillary GC columns were a 42 meter SE-30 SCOT column (SGE) and a 60 meter Carbowax 20 M WCOT prepared for this test study by the dynamic coating method.

Employed for test purposes were practical grade hydrocarbon solutes and lemon oil prepared by a crude extraction of lemon peels with pentane and ether.

The larger volume TCD (160 ul) exhibited an HETP minimum at 80 cm s$^{-1}$ corresponding to a plate number of 28,000. If the FID value is taken as an accurate standard, then the cell volume and cell construction features contribution caused a shift of a factor of 4 (from 20 cm s$^{-1}$) in the ordinate position of the minimum and a factor of 2 loss in maximum plate number achieved (from 58,000 to 28,000). The experimental cell gave results which were nearly identical to the FID curve showing a minimum at ca. 30 cm s$^{-1}$ corresponding to a plate number of 57,000. In addition, the high velocity curves for all cells were coincident. The test results established that a hot wire TCD performance could approach FID sensitivity at optimum flow velocity for the TCD.

We claim:

1. A hot wire thermal conductivity detector cell having an internal free space volume per cavity of less than 50 microliters comprising a cylindrical cavity with
   (a) a first tangential opening in the side wall of said cavity forming a gas entrance port, said first opening being adjacent one end of said cavity, and a second tangential opening in the side wall of said cavity forming a gas outlet port, said second opening being adjacent the other end of said cavity;
   (b) a first pin extending axially from the end of said cavity adjacent the gas inlet port opening to a point beyond the gas inlet port opening, and a second pin extending axially from the other end of said cavity adjacent the gas outlet port opening to a point beyond the gas outlet port opening;
   (c) a filament mounted axially of said cavity on and between said pins,
   whereby the gas entering through the gas inlet port opening flows into a toroidal passage within said cavity and the gas leaving through the gas outlet port flows out from a toroidal passage within said cavity.

2. The cell of claim 1 having an internal volume of less than 25 microliters.

3. The cell of claim 1 wherein the gas flow passageway cross-sectional area of the cavity is less than five times the cross-sectional gas flow area of the entrance port.

* * * * *